United States Patent [19]
Laurila et al.

[11] Patent Number: 5,927,294
[45] Date of Patent: Jul. 27, 1999

[54] METHOD AND PRODUCT SYSTEM FOR PERFORMING TREATMENT OF HAIR

[75] Inventors: Maija Laurila, Espoo; Pirjo Vapaaoksa, Vantaa, both of Finland

[73] Assignee: Carefibres Oy, Espoo, Finland

[21] Appl. No.: 09/068,389

[22] PCT Filed: Nov. 29, 1996

[86] PCT No.: PCT/FI96/00641

§ 371 Date: May 8, 1998

§ 102(e) Date: May 8, 1998

[87] PCT Pub. No.: WO97/20544

PCT Pub. Date: Jun. 12, 1997

[30] Foreign Application Priority Data

Dec. 1, 1995 [FI] Finland ................... 955777

[51] Int. Cl.$^6$ .............. A45D 7/04; A01K 7/09
[52] U.S. Cl. .......................... 132/202; 132/222
[58] Field of Search ................ 132/202, 203, 132/221, 222, 204

[56] References Cited

U.S. PATENT DOCUMENTS

| | | | |
|---|---|---|---|
| 1,455,802 | 5/1923 | Nessler | 132/222 |
| 3,994,417 | 11/1976 | Boedecker | 221/48 |
| 4,655,377 | 4/1987 | Orangeo, Jr. | 132/222 |
| 4,658,839 | 4/1987 | Dallal et al. | 132/222 |
| 4,848,377 | 7/1989 | Bires et al. | 132/222 |
| 5,045,360 | 9/1991 | Kosal et al. | 427/387 |
| 5,085,858 | 2/1992 | Halloran et al. | 132/203 |
| 5,121,762 | 6/1992 | DiPinto et al. | 132/222 |
| 5,246,694 | 9/1993 | Birthwistle | 424/70.12 |
| 5,294,230 | 3/1994 | Wu et al. | 132/203 |
| 5,439,673 | 8/1995 | Murray | 424/70.12 |

FOREIGN PATENT DOCUMENTS

| | | | |
|---|---|---|---|
| 0 325 761 | 8/1989 | European Pat. Off. | |
| 65968 | 4/1984 | Finland | |
| 24 37 672 | 2/1975 | Germany | |
| 2437672 | 6/1977 | Germany | |
| 41 29 769 | 3/1993 | Germany | |
| 4129769 | 3/1993 | Germany | |
| 1476303 | 6/1977 | United Kingdom | 132/222 |
| WO 83/01054 | 3/1983 | WIPO | |
| WO 95/24525 | 9/1995 | WIPO | |
| WO 95/33438 | 12/1995 | WIPO | |
| WO 96/26313 | 8/1996 | WIPO | |

*Primary Examiner*—Paul J. Hirsch
*Attorney, Agent, or Firm*—Louis Woo

[57] ABSTRACT

The invention relates to a method for performing treatment of hair, where an agent such as a reducing agent that acts chemically on the hair is used. The invention employs a flexible carrier material where the agent has been absorbed. The flexible carrier material is packaged in a damp state and stored in a moisture-tight package in the form of a continuous tape. In use, the package is opened and the tape is put into a use package. The carrier material is taken out in pieces of desired sizes from the use package. The invention further relates to a product system for performing treatment of hair, which system includes flexible carrier material packaged in a damp state as well as a moisture-tight package. The carrier material has been packaged in the form of a continuous tape in a moisture-tight package. The product system further includes a use package for dosing the carrier material.

15 Claims, 2 Drawing Sheets

METHOD AND PRODUCT SYSTEM FOR PERFORMING TREATMENT OF HAIR

FIELD OF INVENTION

The present invention relates to a method for performing treatment of hair. The invention relates also to a product system for hair treatment.

BACKGROUND OF INVENTION

In chemical treatment of hair, such as in bleaching or a permanent waving carried out with the help of sulphur bridges reducing agent, the active agent is allowed to act on the hair chemically for a suitable time. The hair treatment operations of this kind are usually performed by dosing a suitable amount of liquid substance to the hair, which substance contains a suitable amount of active agent.

The problem in the use of liquid substances is their correct dosage. In addition to dosage problems, for avoiding a non-uniform effect of the active substance, various protective measures must be taken. Further, there exists the danger that excess liquid gets onto the skin of the person performing the treatment or the person being treated, which in the worst case causes skin irritation and allergy. Depending on the quality of the active agent the handling of liquids may cause also odors.

U.S. Pat. No. 4,848,377 discloses a hair treatment product, which consists of a non-woven fabric and a solution with which it is impregnated and which can be for example some reducing solution commonly employed in permanent waving. The patent suggests among other things the wetting of a continuous tape with a solution containing active agent and its cutting to pieces of predetermined lengths, which are packaged in a damp state, whereby the said pieces are ready for use to be wrapped together with the hair into a desired shape in the permanent treatment. Various spongy or fibrous elastic materials which are capable of retaining a sufficient quantity of fluid, such as paper and non-woven fabric, are mentioned as possible carrier materials.

German Offenlegungsschrift 4129769 in turn suggests the packaging of wetted pieces into packaging materials, which are either disposable or can be used several times.

SUMMARY OF THE INVENTION

The purpose of the invention is to present a method for performing the hair treatment and a corresponding product system, with the help of which the hair treatment carried out by means of impregnated carrier materials can be made more economical, versatile and practical. For achieving this purpose, the method is mainly characterized by taking out from a moisture tight package pieces of desired sizes of flexible carrier material of the hair acting agent. The product system according to the invention relates to the flexible carrier material being packaged in the form of a continuous tape. The solution containing the active agent is impregnated into a carrier material in the form of continuous tape and being packaged in a damp state within packaging material retaining the properties of the active agent. In connection with the use this continuous material is provided to be dosed by the hairdresser at a correct moisture, which is suitable for the effect of the active agent, in pieces of suitable sizes. The packaging of the material in the form of a long tape reduces the packaging costs and the need of material. The amount of material in the package can be dimensioned according the amount required by one permanent waving treatment. Standardized packages of different sizes can be formed for demands which differ in quantity.

The use package employed by the hairdresser can be formed of the original package material as such or with light modifications and can be intended to be disposable. It is for example a package formed of stiff paperboard material, which can be opened and closed for placing or handling the material and which has a dispensing slit and comprises a separate cutting blade to be attached to the package for pulling out the material and for cutting it to pieces of desired sizes as the treatment of hair goes on.

As far as other advantageous embodiments of the invention are concerned, reference is made to the appended dependent claims and the following description.

BRIEF DESCRIPTION OF THE FIGURES

The invention will be described more closely in the following with reference to the accompanying drawing, wherein.

DETAILED DESCRIPTION OF PREFERRED EMBODIMENTS

Figure 1:
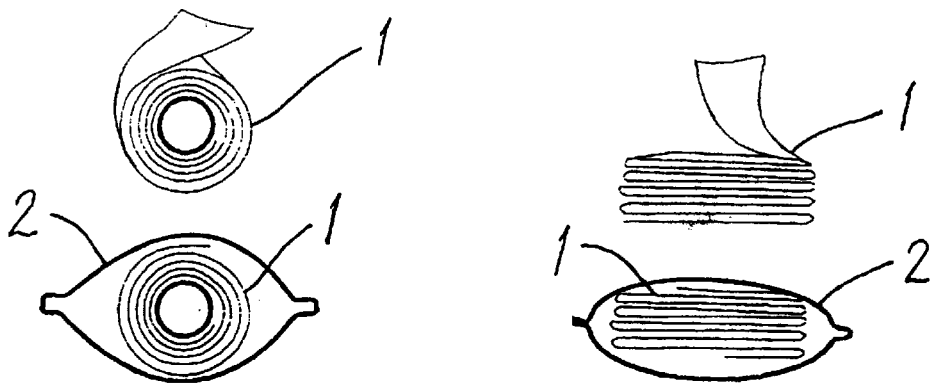
FIG. 1 shows different ways of packaging the carrier material in sectional view.

FIG. 1 shows the carrier material 1 in the form of a continuous tape and having a solution containing an active agent absorbed therein and being placed in an air-tight and moisture-tight packaging material 2. In the examples of FIG. 1 the material is a flexible packaging material forming a pouch- or bag-like package. It can be for example metal foil coated on its inner side with a heat-sealable plastic for closing the packaging material at the seams. Also other packaging materials impermeable to water vapor and oxygen known in the packaging field can be used. The packaging material can be formed also of a hermetically sealable, relatively stiff material, as will be described hereinafter.

The impregnation with the active agent takes place by spraying a suitable amount of the active agent onto a tape-like carrier material located as a roll or in folded configuration in a package bag or in an hermetically sealable package. The package is closed, and the active agent will be absorbed into the material automatically and wets it uniformly. Due to the packaging material, the moisture will not be evaporated from the carrier material, and further, the oxygen of the surrounding air can not affect harmfully the active agent contained in the material, for example by oxidizing a reducing agent.

Figure 2:
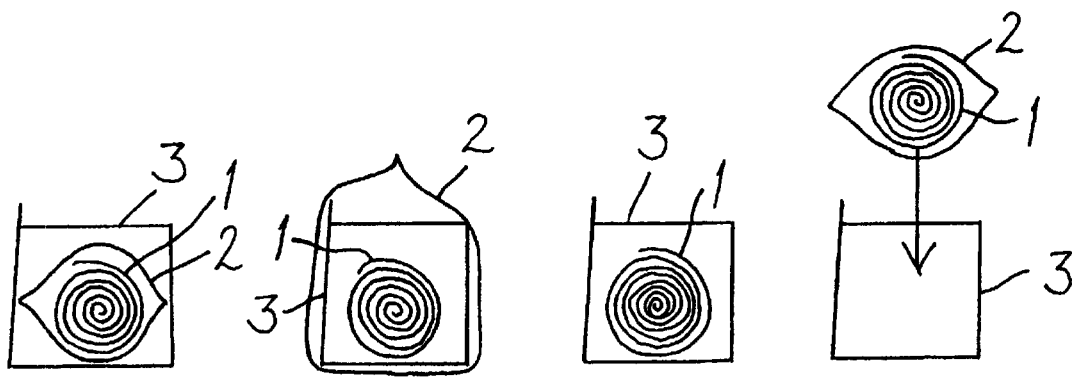
FIG. 2 shows the alternatives for placing the carrier material into the use package in sectional view.

FIG. 2 further illustrates how the product system includes a use package 3, which is used during the hair treatment operation. The carrier material 1 inside the packaging material 2 must be brought to a state of use so that it can be pulled out and cut into sections of desired lengths. The use package 3 is manufactured of a stiff material, such as paper-board, and a cutting blade 5 is mounted thereon. In one wall of the package 3 adjacent to the cutting blade 5 there is further a construction guiding the tape of the carrier material 1, such as a dispensing slit 4.

The part farthest left in FIG. 2 shows an alternative where the packaging material 2 and the carrier material 1 are delivered inside the use package 3 which in this case need not be air-tight. It is sufficient for bringing it to use state to open and remove the bag formed of the packaging material 2, or to leave it opened inside the use package, if it does not make the dispensing of the carrier material 1 difficult. In the following alternative is shown a carrier material 1 placed exposed inside the use package 3, in which case the use package need not be tightly sealed either, because it is surrounded by an outer bag formed of a tight packaging material 2, which can be opened to bring the package to use state. It is followed by an alternative where the use package 3 itself is hermetically closed, in which case a separate tight packaging material 2 is not necessarily needed. Farthest right there is an alternative which differs from previous alternatives showing disposable use packages 3 in that the use package 3 can be employed several times, and the carrier material 1 has been delivered separately inside a tight packaging material 2, and it is placed inside the use package 3 either exposed or in an opened bag formed of a tight packaging material 2.

As the hair treatment is started, the hairdresser opens the package by cutting a metal foil package or other tight packaging material 2 open, or the carrier material 1 can already be in the use package 3, which in this case has been hermetically closed and from which only a closure, such as a closing adhesive strip is torn off. A closure of this kind is most preferably so located that when it is released the dispensing slit 4 or corresponding opening in the use package is made accessible, which can receive the end of the tape-like material. Near the opening on the package there is the cutting blade 5, which can be used for cutting the material pulled out from the opening to pieces of desired lengths. In this way the hairdresser can him/herself determine the sizes of the ready-to-use pieces which shall be placed in contact with the hair.

Figure 3:
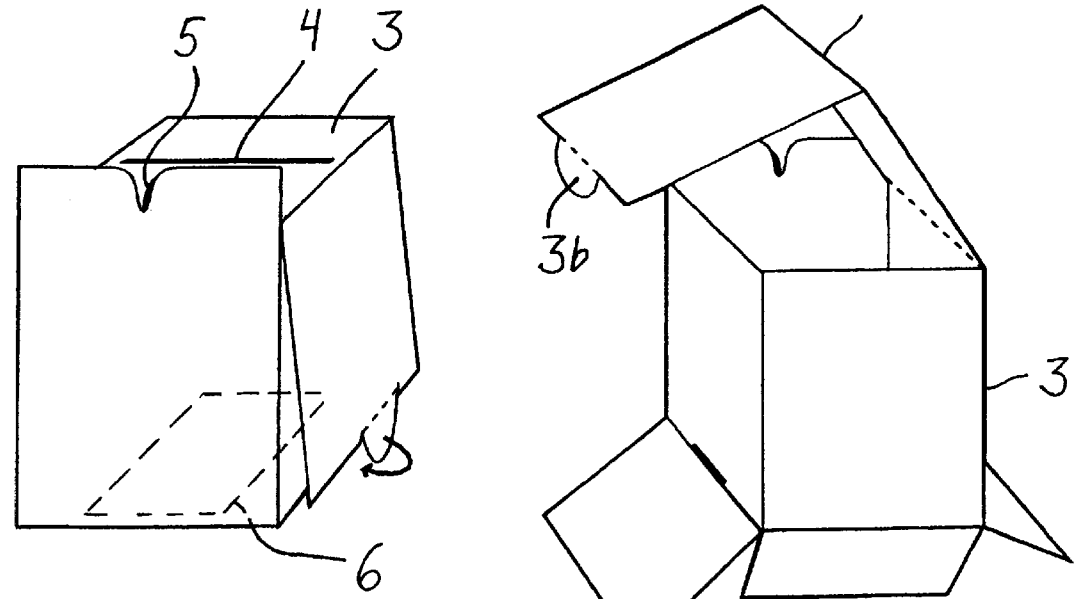
FIG. 3 shows the use package in perspective views.

FIG. 3 shows the use package 3 in perspective view seen from below and from above. The package is a package prepared from a suitable material by folding. One wall of the package is openable for making the package and/or carrier material inside accessible or for placing the carrier material. The front wall of the package continues as a protruding wall part above the top wall comprising the dispensing slit 4. A cutting blade 5 of metal acting as a cutting edge is placed into a recess in the upper edge of this wall part, for example by placing it between two layers of package material in this upper edge. The material of the package can be paperboard material, for example corrugated board or liquid packaging board, which at least on the inside can be coated with a moisture-resistant material, such as thin plastic film. Another alternative is a foldable sheet made of moisture-resistant plastic, such as polypropylene. The cutting blade 5 can accompany the package 3 as a separate piece, and it is mounted into a space reserved therefor before the start of the use, for example into the recess in the front wall, where the sharp cutting edge of the blade is exposed. The downwardly converging shape of the recess guides the material 1 to the cutting edge in the recess. The blade is preferably of special steel used in razor blades which does not interact with the absorbed agents harmfully.

FIG. 3 further shows as a broken line an area 6 on the bottom wall of the package. With the help of this area the use package 3 can be attached to a support 7, such as the help desk of the hairdresser. It can be for example a piece of two-sided adhesive band, and ready-to-use pieces can be extracted with one hand without the need to hold the package.

In the right-hand part of FIG. 3 is illustrated the assembly of the use package 3 by folding from a blank. The vertical side walls can be glued together to form a peripheral construction, and flaps joined to the lower sides can be folded to form a bottom, and a long flap 3a joined to the upper side forms the top wall, which can be folded on the top, and further a wall as an extension thereof, which can be fixed on one side wall by means of a tongue 3b and is releasable for opening the top wall. If hermetical requirements are set to the package 3, the tightness of the seam lines can be ensured for example by methods known in food technology.

Figure 4:
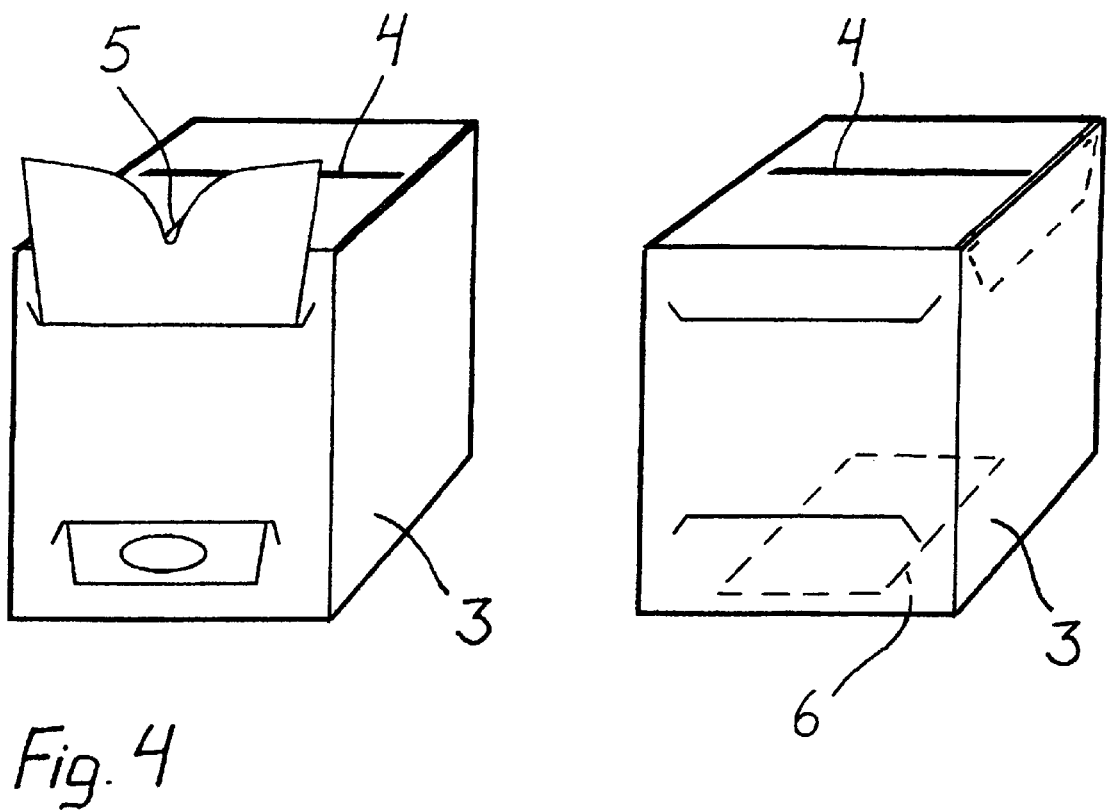
FIG. 4 shows another design of the use package.

FIG. 4 shows another variant of the use package 3. The forming of the package is in the principle the same as in FIG. 3. The dispensing slit 4 is made in the top flap, which can be folded over to form the lid and secured by means of a short tongue at its end which is inserted behind the upper edge of one side wall.

The attachment of the cutting blade with the sharp cutting edge is made by means of a slit, which is below the upper edge of the front wall. The metal blade 5 is attached to a separate plate of e.g. plastic which is inserted in the slit so that its upper part protrudes above the corner between the front wall and top wall. The upper edge of the plastic plate has an approximately V-sharped recess in the middle for guiding the material 1 drawn out of the slit 4 down to the sharp edge of the blade 5 which extends in the recess obliquely with respect to horizontal direction to increase the cutting effect. In the front wall there is also a lower slit from where the lower part of the plate emerges. The front wall area between the slits secures the plate firmly in place. The plate together with the blade 5 is a releasable part and can be easily mounted to the use package 3. The material of the package of FIG. 4 in a practical realization is foldable polypropylene plastic sheet equipped with fold lines.

In the following are presented some appropriate advantageous carrier materials and absorbable substances.

In principle any solution containing an active agent acting chemically on the hair, most commonly an aqueous solution, can be used as the absorbable substance. Such active agents which retain their activity in connection with the carrier material when moist can be used. Active substances used for reducing sulphur bridges of keratin, such as different mercaptans, for example thioglycolates and thiolactates, can be mentioned as examples. The impregnating solution from which the reducing agents are absorbed into the carrier can be for example some known permanent solution with a basic pH, such as "Natural Styling" by Schwarzkopf or some known so-called acid permanent waving substance, for example "Bonacure"(manufacturer Schwarzkopf), "Evolution" (manufacturer Goldwell), or "Vitawell" (manufacturer Wella).

In the case of permanent waving compositions the pH can be in the range of 6.0 to 9.6.

When the hairdresser uses the product system, he/she does not need to handle and dose liquids, which is a time-consuming operation, but the active agent is in a ready-to-use form in the carrier material at correct moisture content. So that the agent could act on the hair, the hair must be suitably wet, generally washed and towel-dry (dried with towel) in order to be best influenced by the agent, but on the other hand not too wet to form a risk of the agent running down.

A suitable absorbent material capable or retaining liquids but capable of releasing it to hair in connection with use can be employed as carrier material. Suitable materials include different constructions constituted of fibers, especially non-woven constructions or non-woven fabrics. The grammage of the material can vary depending on the need, and most commonly it is in the range of 20 to 120 g/m$^2$. Further, the dimensions of the carrier material can vary, for example the width of the tape can lie in the range of 3 to 7 cm. The term "continuous tape" means a material from which several pieces can be separated successively, and the length of such tape is many times, not less than 10 times and most suitably not less than 15 times the width of the tape. The long non-woven tape needs no transverse perforations or corresponding separation lines, it has a uniform structure throughout its length.

When some above-mentioned active agent or some other active agent is absorbed together with an alkaline water solution into a carrier material, an advantageous additional effect is obtained by using a carrier material containing polysilicic acid, known also under general term silicon dioxide. It has been discovered, that at basic pH the polysilicic acid will be released from the carrier material and is transferred to the hair, which has a profitable effect for the general condition of the hair. The pH of the impregnating solution is in this case above neutral, most suitably over 8.0 and most commonly between 9.0 and 9.6. A suitable materials is for example polysilicic acid-containing, cellulose-based fiber, for example a fiber manufactured by viscose method, where the polysilicic acid has been distributed in a suitable form and uniformly in the fiber throughout the same phase with the viscose during the spinning by the addition of waterglass into the viscose which is to be spun. This fiber is commercially available under trademark "VISIL" (manufacturer Kemira Fibers Oy). The manufacturing method of the fiber is described for example in British Patent No. 1064271 and in Finnish Patent No. 91778. The amount of polysilicic acid expressed as $SiO_2$ can be between 10–40 wt-% of the total mass of the fiber.

However, also other materials can be used as carrier materials containing polysilicic acid, especially fibrous materials where the polysilicic acid is uniformly distributed for example by impregnating a fibrous cellulose material with a solution containing polysilicic acid, as for example disclosed in U.S. Pat. No. 4033913.

In the following the transfer of the silicon to the hair when the carrier material according to the invention is used is shown experimentally.

The Determination of Silicon in the Fiber

A basic solution according to a normal permanent waving formulation was made by leaving out the reducing agent that would interfere with the indication reaction, and the pH was adjusted with $NH_3$ to ca. 9.0–9.5. A non-woven fabric piece (6.5×15 cm) consisting of a polysilicic acid containing viscose fiber was soaked in said basic solution for ca. 10 min, and the piece was removed from the solution.

The silicon was indicated in the following manner:
the solution was made acidic, pH 1.3—1.5, with a 2% $H_2SO_4$ solution,
10 ml of ammonium molybdate solution (10%) was added and the mixture was allowed to stand for 5–10 min,
10 ml of a reducing solution ($Na_2SO_3$, 1.8 g/25 ml) was added, and the mixture was allowed to stand for 5–10 min, color was developed slowly starting from a very light green and it grew darker in course of time.

Determination of Silicon in the Hair

A basic solution was made as above.

A hair bundle moistened with water was rolled together with a non-woven fabric moistened with the basic solution around a curler, a film was wrapped around the curler and it was kept for ca. 20–25 min at a temperature of 45° C. The hair was taken out from the curler without rinsing it in between and it was put in water.

The indication of silicon as above:

the color developed more slowly as in the test with bare fiber and it also had finally a lighter green color than above. The presence of silicon in the hair could be detected qualitatively in this way.

In principle any basic impregnating solution containing an active hair treatment agent, with pH above 8.0, most preferably between 9.0 and 9.6, can be used for transferring silicon to the hair, also others than those containing amine nitrogen (as amino groups or ammonium ions) as a part of the active agent for helping the binding of the agent to the said silicon containing fiber through the amine nitrogen. This solution can contain any agent acting chemically on the hair at basic pH, like a keratin reducing agent, or it can be impregnated with only pH adjusting solutions not chemically active on hair, if only silicon treatment at basic pH is desired, whereby the pH adjusting solution serves merely as an agent to contribute to the transfer of silicon to hair.

In the following are shown still some examples illustrating the effect of the moistened material. Even if they exemplify the use of single pieces, it is apparent that the invention will operate also when corresponding pieces separated from a long tape are used.

Examples

Example 1

(Preparation of the Product)

A material containing "VISIL" non-woven fabric 40 g/m$^2$ was prepared by impregnating the material with a solution containing ammonia (a 25%-ic base solution) and thioglycolic acid (a 98%-ic base solution). The non-woven fabric was cut to pieces of approximately 15×5 cm and they were impregnated with the solution just the amount that the liquid did not trickle from the pieces. The liquid was absorbed in this way ca. 2.5 ml. The wetted fiber was wound together with the hairs, which had been moistened with water, around a curler used for permanent waving, a food packaging film was wrapped thereon, and the sample was kept in an incubator, ca. 40° C., for 15–30 min, and the controls at ambient temperature. After the sufficient treatment time the hairs were taken out from the wrap and they were rinsed with a large volume of water (under running water).

Example 2

A material according to Example 1 was prepared using a solution containing 2.5% of ammonia and 7.5% of thioglycolic acid, and the hairs were treated as described in Example 1. Excellent curls were achieved as a result at both treatment temperatures, and the feel of the hairs was better than made in a traditional way. Moreover, the curls were better than achieved by a corresponding method using a commercial product.

Example 3

A material according to Example 1 was prepared using a solution containing 5% of ammonia and 5% thioglycolic acid, and the hairs were treated as described in Example 1. Excellent curls were achieved as a result at both treatment temperatures, and the feel of the hairs was better than made in a traditional way.

Example 4

The material according to Example 1 was dried, the hairs were treated as described in Example 1, and in addition to that, after the winding the non-woven fabric together with the hairs was wetted before heat treatment. The created curl was not as strong as made with the moist non-woven fabric according to Example 1.

Example 5

A material according to Example 1 was manufactured, containing 80 g/m² VISIL non-woven fabric, which was impregnated with a solution containing 5% of ammonia and 15% of thioglycolic acid, and the product was dried. The hairs were treated as described in Example 4. Both treatment temperatures resulted in curls which were not as strong as those made with the moist non-woven fabric according to Example 1.

Example 6

A material according to Example 1 was prepared, but instead of thioglycolic acid, thiolactate (97%-ic base solution) was used, and the hairs were treated as described in the Example 1.

Example 7

A material according to Example 3 was prepared by using thiolactate and by treating the hairs in the way described in Example 1. Still better feeling and better looking curls were achieved as a result compared with the thioglycolate treatment.

The continuous carrier materials of viscose fiber containing polysilicic acid have been impregnated with various commercial permanent-waving formulations, sealed in moisture-proof bags, and before use have been placed in a use package equipped with a cutting blade. According to a professional hairdresser the time for performing permanent waving was shortened clearly compared with the conventional use of liquids and even compared with cutting separate pieces by means of scissors from a continuous material. The extraction of the ready-to-use material from the use package was also quicker than handling of separate pieces each packaged individually in a moisture-proof package.

The invention can be used in connection with all such solutions in liquid form where the active agent retains well its activity in damp state, and it is not restricted only to reducing agents employed in permanent waving.

We claim:

1. A method of performing treatment of hair using an agent such as a reducing agent that acts directly or indirectly on hair, comprising the steps of:
   a) employing a flexible carrier material absorbed with said agent;
   b) packaging said agent absorbed flexible carrier material in a damp state;
   c) packaging said carrier material in the form of a continuous tape in at least one of a moisture tight package or a use package;
   d) packaging said carrier material in the form of a continuous tape in the other of said moisture tight package or said use package; and
   e) taking out said carrier material in pieces of desired sizes from said use package by cutting with a cutting blade included in said use package.

2. Method according to claim 1, wherein said carrier material which is to be used is in the form of a rolled or folded configuration.

3. Method according to claim 1, wherein said carrier material comprises at least partly fibers containing polysilicic acid.

4. Method accordingly to claim 3, wherein said polysilicic acid containing fibers are viscose fibers that contain polysilicic acid.

5. Method according to claim 3, wherein said carrier material is impregnated with a liquid having a pH above neutral, preferably over 8.0.

6. Apparatus for performing treatment of hair, comprising:
   a flexible carrier material in a damp state;
   a moisture tight package whereinto said flexible carrier material is packaged in the form of a continuous tape; and
   a use package having a dispensing slit or opening and a cutting blade attached thereto;
   wherein said carrier material is dispensed from said use package.

7. Apparatus according to claim 6, wherein said flexible carrier material has absorbed thereinto an agent such as a reducing agent that acts directly or indirectly on hair.

8. Apparatus according to claim 6, wherein said carrier material is packaged in the form of a roll or in folded configuration.

9. Apparatus according to claim 6, wherein said carrier material contains fiber containing polysilicic acid, preferably viscose fiber that contains polysilicic acid.

10. Apparatus according to claim 9, wherein said carrier material is impregnated with a liquid having the pH above neutral, preferably over 8.0.

11. A method of performing treatment of hair using an agent such as a reducing agent that acts directly or indirectly on hair, comprising the steps of:
   a) employing a flexible carrier material absorbed with said agent;
   b) packaging said agent absorbed flexible carrier material in a damp state;
   c) packaging said carrier material in the form of a continuous tape in a moisture tight package;
   d) taking out said carrier material in pieces of desired sizes from said use package by cutting with a cutting blade included in said use package.

12. Method according to claim 11, wherein said carrier material which is to be used is in the form of a rolled or folded configuration.

13. Method according to claim 11, wherein said carrier material comprises at least partly fibers containing polysilicic acid.

14. Method accordingly to claim 13, wherein said polysilicic acid containing fibers are viscose fibers that contain polysilicic acid.

15. Method according to claim 13, wherein said carrier material is impregnated with a liquid having a pH above neutral, preferably over 8.0.

* * * * *